United States Patent [19]

Guckel

[11] 4,180,771

[45] Dec. 25, 1979

[54] CHEMICAL-SENSITIVE FIELD-EFFECT TRANSISTOR

[75] Inventor: Henry Guckel, Madison, Wis.

[73] Assignee: Airco, Inc., Montvale, N.J.

[21] Appl. No.: 856,935

[22] Filed: Dec. 2, 1977

[51] Int. Cl.² .................. G01N 27/56; G01N 31/04; A61B 5/05
[52] U.S. Cl. ................................. 324/71 SN; 357/23; 357/25; 128/635; 204/195 G; 204/195 M
[58] Field of Search ............... 357/23, 25; 324/71 SN, 324/29, 30 R; 128/2 E, 2.1 E; 204/195 M, 195 P, 195 G; 27/571

[56] References Cited

U.S. PATENT DOCUMENTS

| 3,311,756 | 4/1967 | Nagata et al. | 357/23 |
| 3,381,432 | 8/1974 | Cox | 73/23 |
| 3,999,122 | 12/1976 | Winstel et al. | 324/71 SN |
| 4,020,830 | 5/1977 | Johnson et al. | 128/2 E |

OTHER PUBLICATIONS

T-Matsuo et al. "An Integrated Field-Effect Electrode for Biopotential Recording" IEEE Trans. Bio-Med. Eng., vol. BME-21, No. 6 pp. 485-487 Nov. 1974.
P. Bergveld, "Development, Operation and Application of the Ion-Sensitive Field Effect Transistor as a Tool for Electrophysiology" IEEE Trans. Bio-Med. Eng. vol BME-19, No. 5, pp. 342-351 Sep., 1972.
Esushi et al. "Integrated Micromulti Ion Sensor Using Field Effect Semiconductor" IEEE Trans. Bio-Med. Eng., vol. BME-25 No. 2 (3/1978).

Primary Examiner—Rudolph V. Rolinec
Assistant Examiner—Walter E. Snow
Attorney, Agent, or Firm—David A. Draegert; Edmund W. Bopp; Roger M. Rathbun

[57] ABSTRACT

The invention relates to an insulated-gate field effect transistor which is adapted for detecting and measuring various chemical properties such as ion activity in a solution. The device has a chemically sensitive layer which overlies a portion of a substrate other than that covered by the gate insulator. When this chemically sensitive layer is exposed to a solution or other substance, the electric field in the substrate is modified which changes the conductance of the channel between a source region and a drain region. The change in conductance is related to the chemical exposure and can be detected with a current meter.

10 Claims, 1 Drawing Figure

U.S. Patent
Dec. 25, 1979
4,180,771
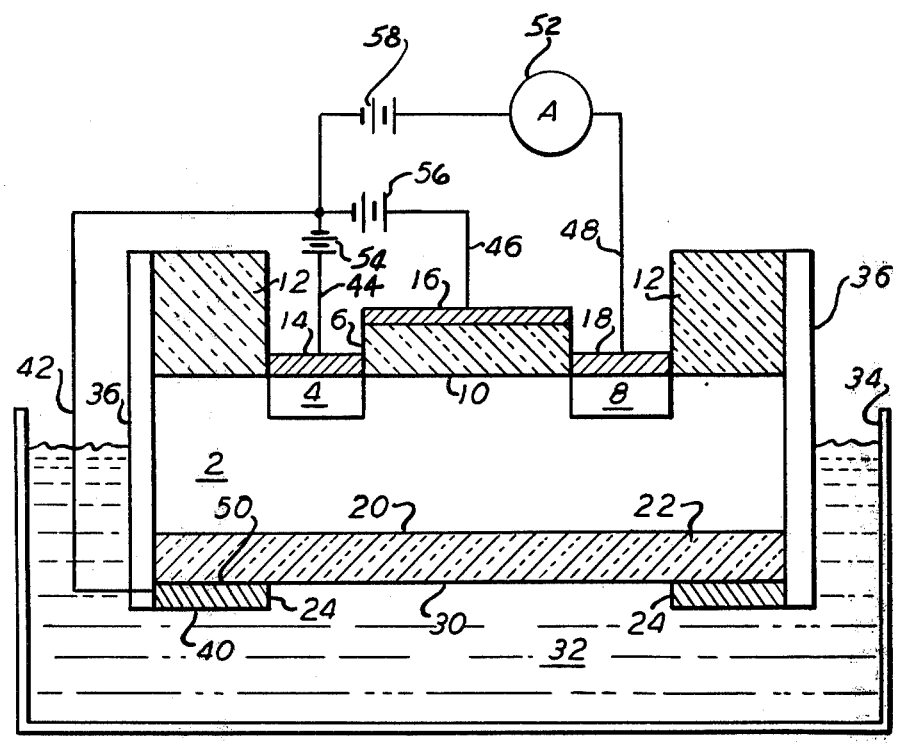

CHEMICAL-SENSITIVE FIELD-EFFECT TRANSISTOR

BACKGROUND OF THE INVENTION

The invention relates to an insulated-gate field-effect transistor which is adapted for detecting and measuring various chemical properties such as ion activity in a solution.

The measurement and monitoring of chemical properties, such as the presence, concentration and activity of particular ions, enzymes, antibodies, antigens, hormones and gases, are important in medical diagnosis and treatment and many other fields. Several attempts to adapt an insulated-gate field-effect transistor (IGFET) to facilitate such measurements have been reported. Among these are the article by P. Bergveld, "Development, Operation and Application of the Ion-Sensitive Field-Effect Transistor as a Tool for Electrophysiology", IEEE Trans. on Bio-Med. Eng., Vol. BME-19, No. 5, pp. 342-351, September 1972; the article by T. Matsuo and K. D. Wise, "An Integrated Field-Effect Electrode for Biopotential Recording", IEEE Trans. on Bio-Med. Eng., pp. 485-487, November 1974; and U.S. Pat. No. 4,020,830, "Selective Chemical Sensitive FET Transducers", issued May 3, 1977 to C. C. Johnson et al.

A conventional IGFET comprises a semiconductor substrate, a source region and a drain region. The source region is spaced apart from the drain region and both are located at or near one surface of the substrate. The region of the substrate between the source and drain is called the channel. The gate insulator is a thin layer of insulating material which covers the surface of the channel. The gate electrode is a layer of metal which covers the gate insulator. When an electric potential is applied to the gate electrode, the electric field in the gate insulator is modified. The electric field attracts or repels charge carriers, electrons or holes, in the adjacent semiconductor material thereby changing the conductance of the channel. The change in conductance of the channel is related to the signal applied to the gate electrode and can be measured by a current meter connected in series with a potential source, the source region, and the drain region.

In the previously mentioned attempts to adapt IGFET's to chemical measurements, the conducting metal layer in contact with the gate insulator of a conventional IGFET was omitted or replaced by an ion sensitive membrane. When the gate insulator or the membrane was exposed to an ionic solution, an electric field was induced in the gate insulator. As in a conventional IGFET, this electric field was sufficient to alter the conductance of the channel between the source and the drain regions.

These prior devices had several disadvantages. First, the gate insulator was a thin layer of silicon dioxide which was in close proximity to the test solution, whether the insulator was directly exposed to the solution or covered with a thin membrane. Because of this proximity, the gate insulator was easily contaminated by the solution. Certain contaminants, such as sodium ions, have a very high mobility in silicon dioxide. Thus, the resistance and other critical properties of the gate insulator were likely to be altered by exposure of the device to a solution. As a result, the response of the device varied greatly with time and exposure.

Second, the electrical contacts to the source and the drain region were also in close proximity to the solution. Contamination of the contacts and the remainder of the device could be limited by a protective layer which was impervious to the solution. However, the sequence and process steps for making the contacts, membrane, and protective layer had to be chosen carefully in order to be compatible.

Finally, the active surface area of the device which could be exposed to the solution was quite small because it was limited by the size of the gate region, i.e., by the short distance between the source and drain regions which was typically 20 $\mu$m.

SUMMARY OF THE INVENTION

The present invention relates to an insulated-gate field-effect transistor which is specifically adapted for measuring various chemical properties, such as the presence, concentration, and activity of various chemical and biological substances. The device is based on the discovery that an IGFET can respond to an electrical signal applied to the substrate as well as a signal applied to the gate electrode.

The device comprises a semiconducting substrate having source and drain regions located near one surface. A gate insulator of an electrically insulating material overlies a first area of the substrate between the source and drain regions where it can be protected from the the test substance. Three separate electrodes allow connection of the gate insulator, source region, and drain region to an external circuit. A layer of a chemically sensitive material overlies a second area of the substrate and has an active surface which can be exposed to the substance. The chemically sensitive material can be a membrane of a material selected for its interaction with a particular ion or other substance, or, perhaps, a specially treated region of the substrate material itself.

The separation of the gate insulator from the chemically sensitive layer separates the electrical and chemical functions of the device and prevents any deleterious effect of the test substance on the gate insulator.

In a preferred embodiment, the chemically sensitive layer lies on the opposite side of the substrate from the gate insulator. In this case, not only are the electrical and chemical functions effectively separated, but the processes for forming the gate insulator and the chemically sensitive layer are virtually independent. Thus, the gate insulator can be optimized with less attention to the peculiarities of the chemically sensitive layer. Further, the side of the substrate having the gate insulator is available for the construction of amplifiers and other signal processors by standard integrated circuit techniques.

Preferably, the device is encapsulated in a protective layer of material which is impervious to the test substance and other environmental factors. The device is readily incorporated into a small probe which can be inserted into a human body to measure medically significant chemical properties. Further, the device may incorporate an attached reference electrode to allow more convenient and more reproducible measurements.

As with conventional IGFET's, the device can be constructed with source and drain regions which are either n-type or p-type semiconductor material. Further, the device can be constructed to operate in either an enhancement mode or a depletion mode.

BRIEF DESCRIPTION OF THE DRAWING

The FIGURE is a cross-sectional view of an insulated-gate field-effect transistor device constructed according to the present invention.

DESCRIPTION OF THE PREFERRED EMBODIMENTS

The electrical portion of the device comprises a substrate, a source region, a drain region, a gate insulator and separate source, drain, and gate electrodes.

The substrate is a semiconductor material such as silicon which is lightly doped so as to have a resistivity of approximately 10 $\Omega$.cm. For an n-type substrate, the silicon is doped with a donor element, such as phosphorus. For a p-type substrate, the silicon is doped with an acceptor element, such as boron.

The source and drain regions are regions of semiconductor material of type opposite to that of the substrate and with a resistivity of approximately 0.01 $\Omega$.cm. The source region 4 and the drain region 8 are located near one surface of the substrate 2, as shown in the FIGURE, and are spaced apart by a distance of approximately 20 $\mu$m.

The gate insulator is a layer 6 of electrically insulating material which overlies a first area 10 of the substrate between the source and drain regions. Typically, the gate insulator is approximately 0.1 $\mu$m thick, 20 $\mu$m wide and 0.1 mm long (normal to the plane of the FIGURE). Some areas of the substrate surface outside the gate insulator are also covered with an insulating layer, such as a layer 12 of silicon dioxide.

The source, drain and gate electrodes are three separate layers 14, 16, and 18 of a conducting material, such as aluminum, which allow electrical contact with source region 4, gate insulator 6, and drain region 8, respectively. Typically, the electrodes are 0.5 $\mu$m thick, 20 $\mu$m wide and 0.1 $\mu$mm long.

The chemical portion of the device comprises a layer of a chemically sensitive material which overlies a second area of the substrate separate from the area of the gate insulator. The sensitive layer and the gate insulator may be separated laterally on the same side of the substrate. However, preferably the chemically sensitive layer and the gate insulator are on opposite sides of the substrate. In the FIGURE, the gate insulator 6 overlies a first area 10 on the upper surface of the substrate 2, and the chemically sensitive layer 22 overlies a second area 20 on the lower surface of the substrate.

The nature of the chemically sensitive material depends upon the substance which is to be detected. For the measurement of hydrogen ion concentration, layer 22 could be a pH glass, such as Corning 0150 glass. For the measurement of potassium ion concentration, layer 22 could be a polymeric membrane comprising polyvinylchloride, a plasticizer and an ion-exchanger, such as the antibiotic valinomycin. Membranes sensitive to other ions, enzymes, antibodies, antigens, hormones, gases, and other substances can be fabricated using known technology. See W. Simone, W. E. Mofr, and P. C. H. Meier, "Specificity for Alkali and Alkaline Earth Cations of Synthetic and Natural Organic Complexing Agents in Membranes", in Structure and Bonding, J. D. Dunitz et al. Ed., Vol. 16, pp. 113–160, Springer-Verlag, New York, 1973; and G. A. Rechnitz, "Membrane Bioprobe Electrodes", C. & E. News, Vol. 53, pp. 29–35, Jan. 27, 1975.

The chemically sensitive layer 22 has an active surface 30 which is to be exposed to the test substance. Preferably the remainder of the device is enclosed in an encapsulating layer 36, only partially shown in the FIGURE, which is impervious to the test substance and other environmental factors. Such an encapsulating layer of glass, epoxy or other material protects the device from contamination and other deleterious effects when the device is exposed to a test substance, as by immersing the device in an ionic solution 32 in a container 34.

When an electrochemical potential in a solution is measured, it is usually desirable to use a reference electrode in order to obtain stable, reproducible results. This reference electrode may be external to the device. However, it is preferred to incorporate the reference electrode into the device, as shown in the FIGURE. The reference electrode 24 may comprise a silver-silver chloride electrode in which one surface 40 of a layer of silver is converted to silver chloride. The silver layer has a contact for an electrical connection, and the silver chloride surface is exposed to the solution. If necessary, the reference electrode can be isolated from the chemically sensitive layer by providing an intermediate layer of an insulator, such as silicon dioxide, as the interface 50 between electrode 24 and layer 22.

In use, the device is connected to an external electric circuit. The circuit is similar to that for prior ion-sensitive IGFET's except that the substrate and source electrode are not connected together, and, if used, the reference electrode is between the solution and gate electrode rather than between the solution and the substrate. For a device with n-type source and drain regions, the source electrode 14 is connected to the positive terminal of a source-bias potential source 54 by a conductor 44. The drain electrode 18 is connected to a current meter 52 by a conductor 48. The current meter is also connected to the positive terminal of a drain-bias potential source 58. The negative terminal of potential source 58 is connected to the negative terminal of potential source 54. The potential sources 54 and 58 are such that the drain electrode 18 is at a positive potential with respect to the source electrode 14. The gate electrode 16 is connected to the positive terminal of a gate-bias potential source 56 by a conductor 46. The negative terminal of the potential source 56 is connected to the negative terminals of the potential sources 54 and 58. A suitable reference potential is provided by a reference electrode 24 which is exposed to the test substances and connected to the common negative terminals of three potential sources 54, 56 and 58 by a contact 42. Thus, the potential source 56 and conductor 46 form an electrical connection between the contact 42 and the gate electrode 16. The potential sources 54, 56 and 58 can be batteries or electronic power supplies. For a device with p-type source and drain regions, the polarities of the potential sources 52, 54 and 56 are reversed. Several variations of the external circuit are known to those versed in the art.

The interaction at the surface 30 between the test substance and the chemically sensitive layer 22 produces an electric potential at the substrate area 20 which modifies the electric field in the substrate 2. In a device with n-type source and drain regions, the charge carriers are predominantly electrons, and a negative potential applied to substrate area 20 increases the conductance of the channel. In a device with p-type source and drain regions, the charge carriers are predominantly holes, and a positive potential applied to substrate area 20 increases the conductance of the channel.

A suitable IGFET device can be produced by a combination of steps which are conventional in the fabrication of metal oxide-silicon devices. First, a suitable silicon wafer is cleaned with organic and inorganic solvents such as trichloroethylene, ammonium hydroxide, and hydrogen peroxide. The cleaned wafer is heated to approximately 1050° C. in a furnace containing an oxygen atmosphere to grow a layer of silicon dioxide approximately 1.5 μm thick.

Conventional photolithographic techniques are used to cut holes in the silicon dioxide where the source and drain regions are to be. Photoresist is applied to the silicon dioxide layer and exposed to light through a suitable mask whiich prevents exposure of certain areas which become the source and drain. The photoresist is developed, baked, and the wafer is etched with a buffered solution of hydrofluoric acid which removes the silicon dioxide from the unexposed areas. The residual photoresist is removed and the wafer cleaned.

The source and drain regions are doped to the desired concentration of an appropriate donor or acceptor element by conventional diffusion processes. The wafer is placed in a furnace containing an atmosphere of a suitable dopant element until the desired amount of the dopant has been introduced into the substrate. After the portion of the silicon dioxide layer which contains dopant material is removed, the wafer is placed into a diffusion furnace for a time and temperature appropriate to diffuse the dopant material into the substrate to form source and drain regions of the desired depth, such as 2 μm. The wafer is heated in an oxygen atmosphere to regrow silicon dioxide over the source and drain regions.

A hole for the gate is cut by conventional photolithographic techniques similar to those used to cut the holes for the source and drain regions. The hole for the gate is cut completely through the existing oxide layer. The gate insulator is then grown to a thickness of approximately 0.1 μm by heating the wafer in an oxygen atmosphere. Precise control of the thickness and other properties of the gate insulator is essential to obtain devices of uniform characteristics.

After appropriate holes are cut, the source, drain and gate electrodes are formed by depositing a layer of aluminum, chromium, nickel, gold or other suitable conductor by a conventional process such as vacuum evaporation or sputtering. The desired pattern of separate electrodes is established by applying photoresist and etching away undesired portions of the metal layer. In the case of an aluminum layer, phosphoric acid is a suitable etchant.

At some time, either before or after formation of the gate insulator, a layeer of a chemically sensitive material is placed on the substrate. The particular technique for forming the layer depends upon the nature of the chosen material. In the case of a pH glass, the layer can be attached with an adhesive, by electrostatic bonding, or deposited by radio-frequency sputtering. See the article by Y. Saito et al, entitled "The RF Sputtering Technique as a Method for Manufacturing Needle-Shaped pH Microelectrodes", pp. 103-9, of Ion and Enzyme Electrodes in Biology and Medicine, M. Kessler et al, Ed., University Park Press, Baltimore 1976. A polymeric membrane can be deposited from a solution by evaporation of the solvent. The device can be encapsulated in a conventional manner as long as an opening is provided to allow exposure of the active surface 30 to the test substance.

If a reference electrode is incorporated into the device, it may be formed by conventional techniques. For example, a silver-silver chloride electrode is formed by depositing a layer of silver by vacuum evaporation, and treating one surface with a concentrated solution of sodium chloride to form a silver chloride layer. If necessary, the reference electrode can be isolated from the chemically sensitive layer by thermally growing a layer of silicon dioxide on the surface 50 between the electrode 24 and layer 22.

A typical device occupies an area of approximately 0.1×0.1 mm on a wafer which is approximately 0.1 mm thick. Of course, a large number of devices can be made at one time on a single wafer. The devices can then be separated, interconnected, and encapsulated as desired. Because of their small size, one or more devices can be incorporated into tiny probes which can be inserted into delicate regions of a human body or other difficult to reach and easily disturbed locations. Such probes can be combined with an external circuit similar to that shown in the FIGURE to form an instrument for measuring a medically significant property such as the pH of blood.

What is claimed is:

1. A field-effect transistor device for measuring a chemical property of a substance to which the device is exposed, comprising:
   a semiconductor substrate;
   a source region in contact with the substrate and located near a first surface of the substrate;
   a drain region in contact with the substrate, located near the first surface of the substrate and spaced apart from the source region;
   a gate insulator which overlies a first area of the first surface of the substrate between the source and drain regions;
   three electrodes for providing a separate electrical connection to the source region, drain region, and gate insulator; and
   a layer of chemically sensitive material which overlies a second area of the substrate separate from the first area and which has an active surface for exposure to the substance, said chemically sensitive material connected in series with the substrate and located on the opposite side of the substrate from the gate insulator, said second area located sufficiently near the source and drain regions so that exposure of the chemically sensitive material to the substance results in a change of the electrical conductance between the source and drain regions.

2. The device of claim 1 in which the chemically sensitive material lies on the substrate directly opposite the gate insulator.

3. The device of claim 2 further comprising an encapsulating layer of a material which is impervious to the test substance and which has an opening to allow exposure of the active surface.

4. The device of claim 2 further comprising:
   a reference electrode attached to the device on the same side of the substrate as the chemically sensitive material and having a surface for exposure to the substance; and
   a contact for making an electrical connection to the reference electrode.

5. The device of claim 2 wherein the chemically sensitive material is a membrane which interacts with a particular kind of ion when exposed to a solution containing such ions.

6. The device of claim 5 wherein the membrane is a pH sensitive glass.

7. The device of claim 5 wherein the membrane is a polymeric material containing an ion-exchanger.

8. The device of claim 1 comprising a probe for insertion into the human body.

9. The device of claim 4 comprising an instrument for measuring a medically significant chemical property in a human body, and further comprising:

an electric circuit which includes
a potential source and a current meter connected in series with the source electrode and the drain electrode, and
an electrical connection between the contact of the reference electrode and the gate electrode.

10. The device of claim 1 wherein the three electrodes are all on the same side of the substrate and the chemically sensitive material is on the opposite side of the substrate from that of the three electrodes.

* * * * *